(12) United States Patent
Juhnke et al.

(10) Patent No.: US 11,646,036 B1
(45) Date of Patent: May 9, 2023

(54) TEAM MEMBER IDENTIFICATION BASED ON PSYCHOGRAPHIC CATEGORIES

(71) Applicant: HUMANCORE LLC, Northbrook, IL (US)

(72) Inventors: Joseph Juhnke, Evanston, IL (US); Mark Farnham, Northborok, IL (US)

(73) Assignee: HUMANCORE LLC, Northbrook, IL (US)

( * ) Notice: Subject to any disclaimer, the term of this patent is extended or adjusted under 35 U.S.C. 154(b) by 0 days.

(21) Appl. No.: 17/589,668

(22) Filed: Jan. 31, 2022

(51) Int. Cl.
*G10L 17/04* (2013.01)

(52) U.S. Cl.
CPC .................................. *G10L 17/04* (2013.01)

(58) Field of Classification Search
CPC ... G10L 2015/027; G10L 15/01; G10L 15/02; G10L 15/16; G10L 15/18; G10L 17/04; G06N 20/00
USPC .................................................. 704/231, 257
See application file for complete search history.

(56) References Cited

U.S. PATENT DOCUMENTS

| | | | | |
|---|---|---|---|---|
| 9,390,378 | B2 * | 7/2016 | Garera | G06Q 10/101 |
| 10,108,932 | B2 * | 10/2018 | Sung | G06Q 10/1053 |
| 10,387,467 | B2 * | 8/2019 | Allen | G06F 16/337 |
| 10,885,530 | B2 | 1/2021 | Mercury et al. | |
| 2004/0225535 | A1 * | 11/2004 | Bond, Jr. | G06Q 40/02 705/4 |
| 2010/0332281 | A1 * | 12/2010 | Horvitz | G06Q 10/06311 705/7.26 |
| 2012/0095585 | A1 * | 4/2012 | Agarwal | G06Q 10/06 700/109 |
| 2012/0296682 | A1 * | 11/2012 | Kumar | G06Q 10/00 705/7.11 |
| 2013/0254787 | A1 * | 9/2013 | Cox | H04N 21/252 725/13 |
| 2014/0017677 | A1 | 1/2014 | Yu et al. | |
| 2014/0129463 | A1 * | 5/2014 | Grayevsky | G06Q 10/1053 705/321 |
| 2014/0129464 | A1 * | 5/2014 | Grayevsky | G06Q 10/1053 705/321 |
| 2015/0058004 | A1 * | 2/2015 | Dimitriadis | G10L 25/78 704/233 |
| 2015/0264438 | A1 * | 9/2015 | Cox | H04N 21/25883 725/10 |
| 2015/0339630 | A1 * | 11/2015 | Grayevsky | G06Q 10/1053 705/321 |
| 2016/0142754 | A1 * | 5/2016 | Kouritzin | H04H 60/45 725/14 |

(Continued)

*Primary Examiner* — Akwasi M Sarpong
(74) *Attorney, Agent, or Firm* — Troy Smith (57) ABSTRACT

Systems, methods, and computer-executable instructions for identifying a candidate include receiving unscripted communication, the unscripted communication comprising communication from a first speaker. Properties of the unscripted communication are extracted. A psychographic classifier classifies the first speaker into a psychographic category based on the extracted properties. An aggregate psychographic category of a team is determined based on psychographic categories of each of the team members of the team. A weakness in the aggregate psychographic category of the team is determined. A new team member that has a psychographic category that addresses the weakness in the aggregate psychographic category of the team is identified. A recommendation that the first speaker become a team member of the team is provided.

20 Claims, 6 Drawing Sheets

(56) References Cited

U.S. PATENT DOCUMENTS

| | | | |
|---|---|---|---|
| 2016/0203433 A1* | 7/2016 | Chen | G06Q 10/063112 |
| | | | 705/7.14 |
| 2016/0267425 A1* | 9/2016 | Li | G06Q 10/0631 |
| 2017/0154314 A1* | 6/2017 | Mones | G06N 20/00 |
| 2017/0236150 A1* | 8/2017 | Fiderer | G06Q 30/0251 |
| | | | 705/14.49 |
| 2017/0270544 A1* | 9/2017 | Jaidka | G06Q 30/0202 |
| 2018/0027118 A1* | 1/2018 | Sharpe | H04M 3/42068 |
| | | | 379/265.11 |
| 2018/0082258 A1 | 3/2018 | Mather et al. | |
| 2018/0152506 A1* | 5/2018 | Simó | G06Q 10/06 |
| 2018/0253297 A1* | 9/2018 | Richardson | G06F 40/169 |
| 2018/0260860 A1* | 9/2018 | Devanathan | G06F 16/353 |
| 2018/0350389 A1* | 12/2018 | Garrido | G10L 25/48 |
| 2019/0213498 A1* | 7/2019 | Adjaoute | G06N 3/126 |
| 2019/0236511 A1* | 8/2019 | Xu | G06F 9/485 |
| 2019/0251516 A1* | 8/2019 | Champaneria | G06F 16/951 |
| 2019/0303829 A1* | 10/2019 | Sheu | G06Q 10/06315 |
| 2019/0318407 A1* | 10/2019 | Giridhari | G06Q 30/0627 |
| 2020/0019609 A1* | 1/2020 | Yu | G06N 3/0445 |
| 2020/0097481 A1* | 3/2020 | Cosentino | G06F 16/24575 |
| 2021/0056512 A1* | 2/2021 | Misra | G06Q 10/06398 |
| 2021/0279688 A1* | 9/2021 | Boddapu | G06Q 30/0217 |
| 2021/0342554 A1* | 11/2021 | Martin | G06Q 10/0639 |
| 2021/0390878 A1* | 12/2021 | Lee | G06N 5/022 |
| 2022/0001880 A1* | 1/2022 | Giersch | B62D 65/00 |

\* cited by examiner

TEAM MEMBER IDENTIFICATION BASED ON PSYCHOGRAPHIC CATEGORIES

BACKGROUND

From small to large companies, creating teams with the right personnel can be a difficult task. One area of difficulty is selecting team members from potential members that have different experience levels and personalities. Competitive performance of teams may suffer when sub-optimal teams are created. In addition, team communications may be ineffective or inefficient. Current solutions rely on the strengths and experiences of managers to select team members. Such solutions, however, suffer from lack of objective criteria and fail to utilize various data points, which may not even be recorded.

DETAILED DESCRIPTION

Companies have a wealth of talent in its employee pool. Identifying individuals with certain skills and traits, however, is not an easy task. Historically, companies have relied on individual managers to determine the strengths of individuals and how to organize effective teams. Ineffective teams may result in competitive performance suffering and both ineffective and inefficient team communications. Ineffective teams may cost companies a substantial amount of money. In addition, a misstep in hiring may cost a company one-third of the employee's salary or more. Data analysis is not something that has typically been employed in making these decisions.

Various examples disclosed herein describe an employee data analysis suite that identifies the best talent, the right people in the right role, and that teams are comprised of the right individuals. In addition, examples describe how analysis can be employed to determine the strengths of applicants. Through data collection and data analysis, individuals can be identified that have strengths that are missing or not optimal for a team or organization. Identifying individuals that compliment and enhance an existing team or organization is a benefit of the disclosed examples.

In one specific example, the classifier is an artificial intelligence classifier that is trained on a set of classified individuals. In this example, the classifier is based on three centers of intelligence: head, heart, and body. For example, the classifier may classify an employee or team based on the following styles: challenger; peacemaker; reformer; helper; achiever; individualist; investigator; loyalist; and enthusiast. Additional layers can be used to identify finer grained styles. For example, a smaller granularity of styles may include: participation; fusion; worry; rigidity; zeal; privilege; ambition; seduction; security; prestige; charisma; competition; shame; tenacity; safety; seclusion confidence; warmth; duty; strength; loyalty; sacrifice; suggestibility; satisfaction; solidarity; possession; and comfort. In some examples, the classifier creates a fingerprint that provides a score for each style. As detailed in FIG. 3 and FIG. 4, a fingerprint may be created by connecting the scores of the styles.

In various examples, the disclosed system classifies an employee. For example, the classification can be a psychographic classification. As another example, the classification may be a combination of different classifications systems, such as IQ classification, personality typing, Myers-Briggs, DISC, etc. In another example, there may be a classifier for each of a number of possible styles. In this example, an individual may be classified multiple times, one for each relevant style. Based on the classification, an employee or team may be provided with tools and information that can nurture the employee's or team's intelligence, personality, and emotional health. Various examples include psychographic employee and candidate screening; team dynamics analysis and optimization; and hyper-targeted employee assistance and growth. Further, various exemplary systems ensure that hiring decisions meet various applicable rules to ensure equality in a company's hiring process.

Various examples include psychographic employee and candidate screening. In these examples, bias in the hiring process is eliminated. In addition, top performing employees or candidates may be identified. Conversely, lower performing employees may be determined. Based on the psychographic profiles of these employees, additional training material or communication corrections or recommendations may be provided. As another example, once top performing employees are determined, candidates that are similar to these employees in regard to their psychographic profile may be identified as a potential top performer.

Various examples may also include team dynamics analysis and optimization. For example, a psychographic profile of each team member may be determined. These psychographic profiles may then be combined to form a team psychographic profile. For example, the average score for styles may be calculated as the team psychographic profile. As another example, a weighted average may be calculated for each style based on roles or participation of team members. Once the team profile is created, blind spots and strengths of a team are identified. In various example, new team members that address an existing team's blind spots may be searched for and recommended for inclusion on the team. Team communication may also be augmented based on the team's profile or team member profiles. For example, a team member may have an email to the team analyzed. This analysis considers the team's profile and how best a message should be communicated to the team based on the team's profile. Analysis of the content of the email may reveal how the message within the email may be communicated more effectively to the team. These recommendations may be automatically done or may receive permission from the sender to take effect. As described in greater detail, the communication between the team members may be analyzed. This additional analysis may be used to update a team member's psychographic profile, which in turn, may be used to update the team's psychographic profile. Trends and how effective training or recommendations, therefore, may be monitored based on changes of the team's psychographic profile.

Various examples may also include targeted employee assistance and growth. An employee's psychographic profile may be analyzed to determine what assistance may be provided to the employee to address a weakness in the psychographic profile. As another example, communication between two employees with different psychographic profiles may be monitored. Before a chat is sent from one employee to another, the content of the chat may be analyzed. This analysis may use the recipient's psychographic profile to determine if there is a better or alternative way to deliver the content. For example, the recipient may have a high score of a warmth style. Based on this, the current chat, as well as previous communications that are part of the chat, may be analyzed to determine if the sender is being warm. If the analysis determines that the sender is not being warm in their communication, a suggestion to add some warm messaging to the communication may be provided. In another example, the suggestion may include a specific warm message to include. As another example, before the thread of communication has started, the sender or initiator's psychographic profile may be compared with the recipient or recipients' psychographic profile. If the sender scores low on the charisma style and the receiver scores high on the prestige side, a recommendation to provide a compliment to the receiver or praise to the team may be provided. If the sender's score for charisma was high then this recommendation may not be provided. In another example, if the sender's past communication with the receiver included communication that addresses the prestige style of the sender then the recommendation could be skipped. If such past communication, however, was not present the recommendation may be provided.

Figure 1:
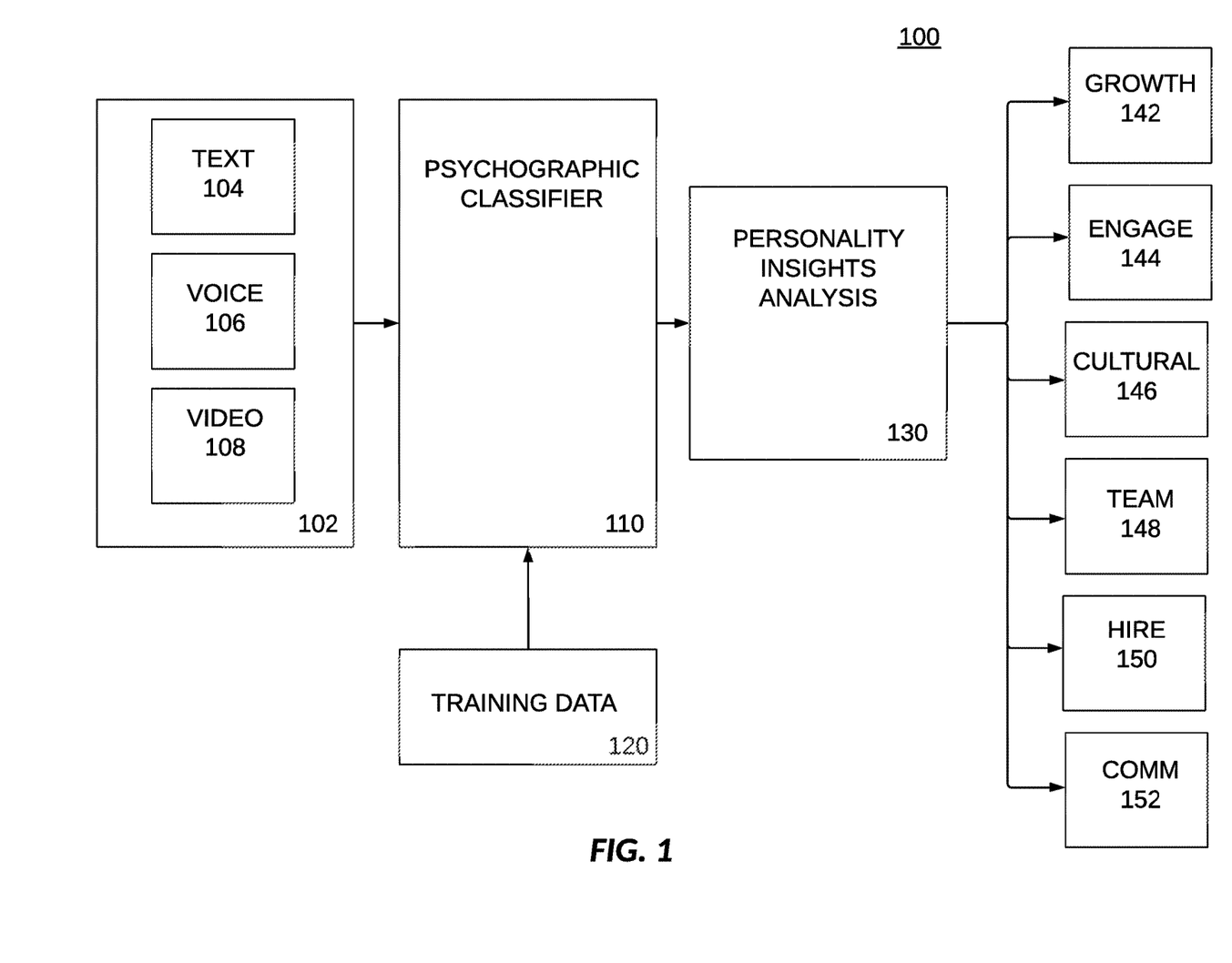
FIG. 1 is a system diagram of a classification system in accordance with respective examples.

FIG. 1 is a system diagram of a classification system 100 in accordance with respective examples. The system 100 includes a psychographic classifier 110 that is trained on training data 120. The training data 120 may include data regarding classified individuals. For example, a certain number of individuals may take a psychographic test. The results of this test may include scores regarding the various psychographic styles of the individual. In addition, communication associated with the individuals may be included in the training set. The training data 120 may also include communication threads between the classified individual and other classified individuals. Features from the communication threads between classified individuals may help determine features relating to how different psychographic styles communicate. The day and time the communications was sent, received, read, or replied to may also be included in the training data 120. In various examples, the training data 120 may also include the location of the individual where the communication was captured. This location feature of the training data 120 may help identify how psychographic styles communication in different locations such as when in a professional setting, driving, or at home.

Various features of the training data 120 may be extracted. The features may be based on the data contained within the training data 120, such as speaker, psychographic scores of the speaker, location, time of day, day of the week, etc. The psychographic classifier 110 may then be trained to classify an unclassified individual based on these features. Bias may be present in the training data 120. If the bias is not addressed, the classifier 110 may utilize this bias in classifying individuals. In some examples, to address bias patterns in classified individuals are determined. For example, use of certain words may classify an individual as aggressive. These words may then be reviewed to determine an actual connection between the use of the word and a classification of being aggressive. If there is no connection between the words and the classification, then those words may be removed from the training data 120 and from the communications 102.

Once trained, the psychographic classifier 110 may be provided with communications 102. The communications 102 may be natural, unscripted communications. For example, the communications 102 may include text 104, voice 106, video 108 data, or any combination therein. The text 104 may include data from emails, chat, social media, etc. Features of text data may include word choice, grammar, length of sentences, tone, etc. The voice 106 data may include recorded presentations, team meetings, phone calls, VOIP recordings, ambient conversations, etc. Features of the voice data may include the text features of the extracted text, the volume of the speaker, changes in volume, tone, interruptions of other speakers, amount of active listener when the speaker is not speaker, etc. The video 108 data may include recorded meetings, presentations, video conferencing, etc. Features of the video data may include the audio features, eye contact when speaking, eye contact with listening, gestures of the speaker, facial expressions of the speaker, etc. Additionally, features extracted from the training data may also be extracted from the communications 102. The unscripted communications may include data from multiple individuals. In these examples, speaker identification may be done to determine who is taking part in various communications, who is speaking, and who is listening.

In an example, the various features are extracted from the communications 102. The features may then be provided to the psychographic classifier 110 to classify individuals. The psychographic classifier 110 may provide a score for each of multiple personality styles for an individual. In various examples, these scores are the individual's psychographic profile. The psychographic profiles of one or more individuals may be analyzed or monitored by a personality insights analysis system 130. This system 130 may monitor changes to psychographic profiles in real-time as the psychographic profiles change based on additional communication that is provided to the psychographic classifier 110. The analysis 130 may include various features. One result of the analysis may be identification of features for employee growth 142. For example, the employee's psychographic profile may indicate areas that training would be the most beneficial. In an example, the psychographic profiles of the employee's boss, colleagues, or staff may be analyzed in combination with the employee's psychographic profile to identify areas of growth for the employee that would have the biggest impact on colleagues.

Similar analysis may be done to identify areas for employee engagement 144 and cultural development 146. For example, a psychographic profile of the entire company or a group within the company may be determined. The psychographic profile of an employee may be compared to the aggregate psychographic profile to determine areas where the employee can grow to be more aligned with the aggregate psychographic profile. Accordingly, an employee may receive training and feedback that better aligns the employee with the existing company culture and increases the engagement of the employee. This analysis may also be done with an aspirational psychographic profile. For example, a company may want to activity shift its culture by increasing more satisfaction, confidence, safety, and loyalty of its employees. An aggregate psychographic profile of all employees, groups of employees, all management employees, or c-suite employees may be determined. Analyzing this aggregate psychographic along with the aspirational psychographic profile may indicate areas where the employees need motivation or training. Providing such motivation and training results in the company's culture towards the aspirational psychographic profile.

Another analysis that may be done is team analysis 148. The team analysis 148 may be used to determine how well a team is likely to perform based on the team's aggregate psychographic profile. For example, the aggregate psychographic profile may indicate that the team has a weakness in that its members all have low participation styles. Once this weakness has been identified, the psychographic classifier 110 may be used to correct this weakness. For example, the team may be expanded to include someone with a high participation style. The classified employees may be searched for potential team members that all have a high participation style. Team member candidate's psychographic profiles may then be compared with the team's aggregate profile to determine each candidate's impact to the team's psychographic profile. A candidate may be recommended to join the team based on the high participation style or the high participation style and how the candidate impacts the team's aggregate psychographic score. For example, two candidates may both have relatively high participation styles. One of the candidates, however, also has a style that positively impacts the team's aggregate score by having styles with scores that are higher than the team's corresponding scores. The other candidate may be more similar to the current team, such that this team member is not the recommended team member. While increasing style scores has been discussed, some styles may benefit from lower scores. In these examples, decreasing the corresponding score would indicate a better candidate to join the team.

Another analysis that may be performed is a new hire 150 analysis. As a company may receive 100s or 1000s of resumes for an opening, the new hire 150 analysis may help reduce the number of applicants by identifying a pool of candidates that best fits a desired psychographic profile. The desire psychographic profile may be an aggregate psychographic profile generated from a group of employees. The group of employees may be a group of high performing employees. The group of employees may also be from a team that the candidate will be joining. In another example, the aggregate psychographic profile is generated from the team's aggregate profile. For example, similar to the team candidate identification above, the desired psychographic profile for candidates may address weaknesses identified in the group. In various examples, while identifying candidates the number of candidates selected based on race or gender may be determined. If the group of selected candidates violates a policy or a rule, the group may be expanded or selectively reduced to align the candidate pool accordingly.

Another analysis that may be performed is communication 152 analysis. The communication 152 analysis may recommend changes to a communication or automatically refine a communication based on psychographic profiles. For example, the receiver's psychographic profile may be used to refine a communication to increase the change that the sender's message is more easily heard by the receiver. For example, a receiver that has a high sacrifice style score may have a message intended for the receiver modified to highlight or emphasize the receiver's sacrifice. As a specific example, a sender may draft a message to the receiver that the team had recently experienced a successful launch of a product. Based on previous communications involving the receiver that indicates that the receiver worked long hours, the message may be refined to provide an explicit acknowledgement of the effort that the receiver put into the successful launch. In another example, a recommendation may be provided to the sender to include. The basis for the recommendation may also be provided to the sender. The sender may then determine to include the recommendation or may tailor the recommendation accordingly.

Figure 2:
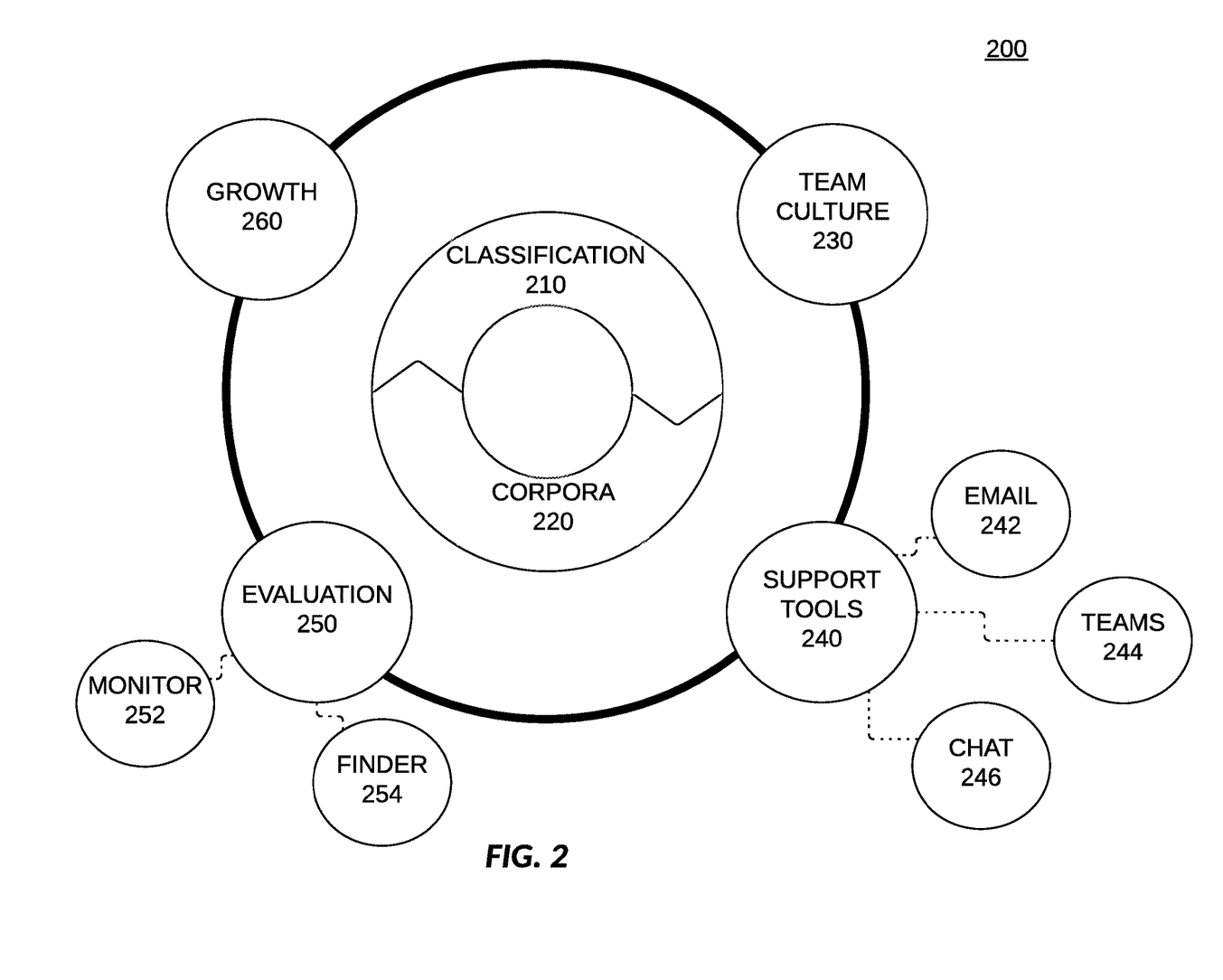
FIG. 2 is a diagram illustrating various components of a classification system in accordance with respective examples.

FIG. 2 is a diagram illustrating various components of a classification system 200 in accordance with respective examples. The classification system 200 is an example of the classification system 100 but illustrated slightly differently. Corpora 220 may be continuously expanded based on input from support tools 240. For example, the support tools 240 may include email 242, team communications 244, and chats 246. Emails 242 may be provided from known email servers and clients. In some examples, plug-ins for existing tools may be used to collect relevant data for the corpora 220. Team communications 244 may comprise recorded meetings. The chats 246 may include team chats. A psychographic classifier may make classifications 210 based on the corpora 220. Evaluation 250 may be done by evaluation bots. The evaluation bots may monitor changes to the psychographic profiles of individuals, teams, organizations, etc. Changes found may be communicated and reported upon. Certain changes may be used to trigger the reporting of the changes. The evaluation 250 may also be used to identify high performing employees. Team culture 230 may be analyzed based on the psychographic profiles of the team members. Individual growth 260 may also be monitored based on the psychographic profiles of individuals. As explained above, training and input regarding communications may be provided to individuals based on their psychographic profiles or psychographic profiles of others. This training and input may be designed to help the individual improve their communication style and effectiveness.

Figure 3:
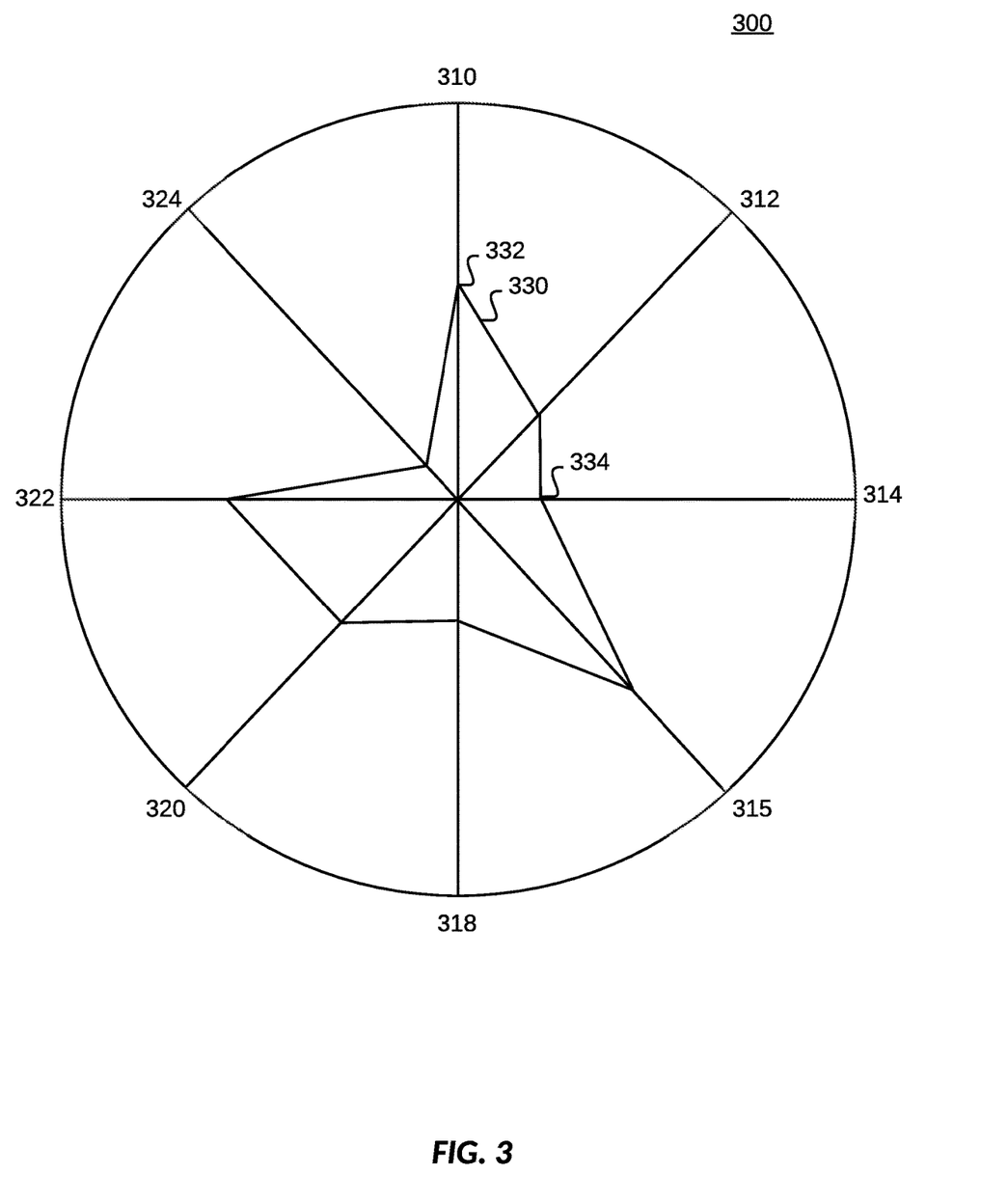
FIG. 3 is a diagram illustrating a fingerprint of an individual in accordance with respective examples.

FIG. 3 is a diagram illustrating a fingerprint 300 of an individual's psychographic profile in accordance with respective examples. In this example, there are eight different styles 310, 312, 314, 316, 318, 320, 322, and 324. An individual may be classified for each of the eight different styles using one or more classifiers. The score for each of the styles may be visually graphed 330 to show an individual's strengths and weaknesses. For example, the style 310 may represent a peacemaking style. The individual has a high peacemaking style score 332. Style 314 may indicate a helper style, where the individual is relatively weak 334. In addition to determining a psychographic fingerprint of an individual, the system may provide a detailed summary of the psychographic profile. This profile may be based on all or a subset of style scores for an individual. For example, all of the styles may be used to determine the psychographic profile of an individual.

The profile may include a name for the type of profile, an overview of the profile, and a listing of strengths. In addition, the needs and wants of the profile may be provided. These needs and wants indicate what motivates individuals that are classified as this type of profile. The profile may include additional information providing insights into how best to communicate and interact with an individual. For example, the profile may include drives, fears, desires, beliefs, likes, dislikes, triggers, challenges, guidance, etc. The profile may also include insights on how this individual works within groups and keys for growth. This profile may be used be the various analyses discussed above. For example, the profile may be used to determine how best two individuals should communicate. In this example, the profiles of the individuals that are communicating may be used to determine recommendations for communications.

Figure 4:
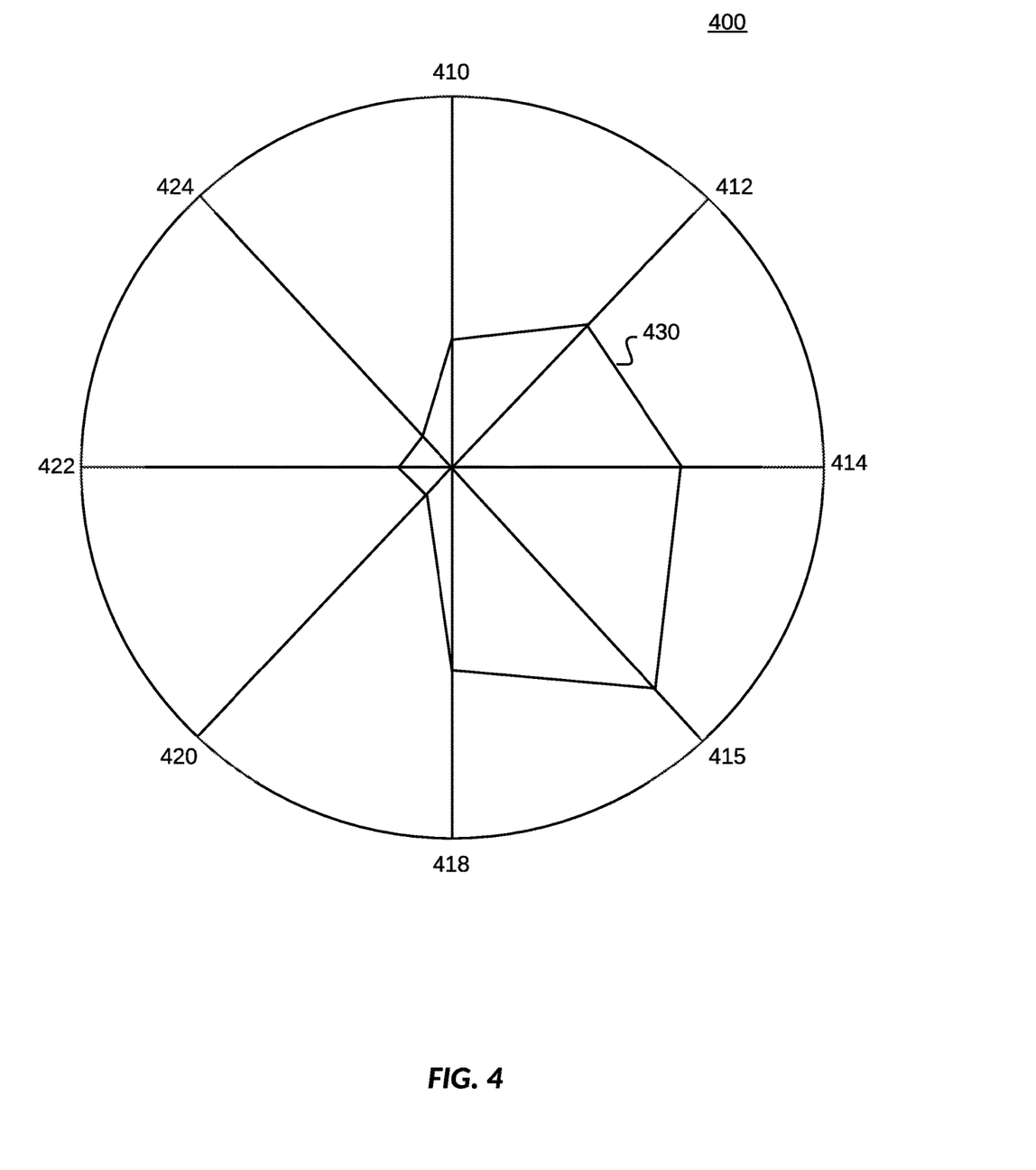
FIG. 4 is a diagram illustrating an aggregate fingerprint of multiple individuals in accordance with respective examples.

The fingerprint concept is not limited to individuals. The fingerprints of multiple individuals may be aggregated into a group's fingerprint. FIG. 4 is a diagram illustrating an aggregate fingerprint 400 of multiple individuals in accordance with respective examples. Similar to FIG. 3, the fingerprint 400 may include eight different styles 410, 412, 414, 416, 418, 420, 422, and 424. Fingerprints are not limited to eight styles and may consist of fewer styles or more styles. For example, a fingerprint may include 3, 6, 9, 27, etc., styles. The score for each of the styles may be graphed to show the aggregate score 430 for the group. The group's fingerprint may be used as described herein.

Figure 5:
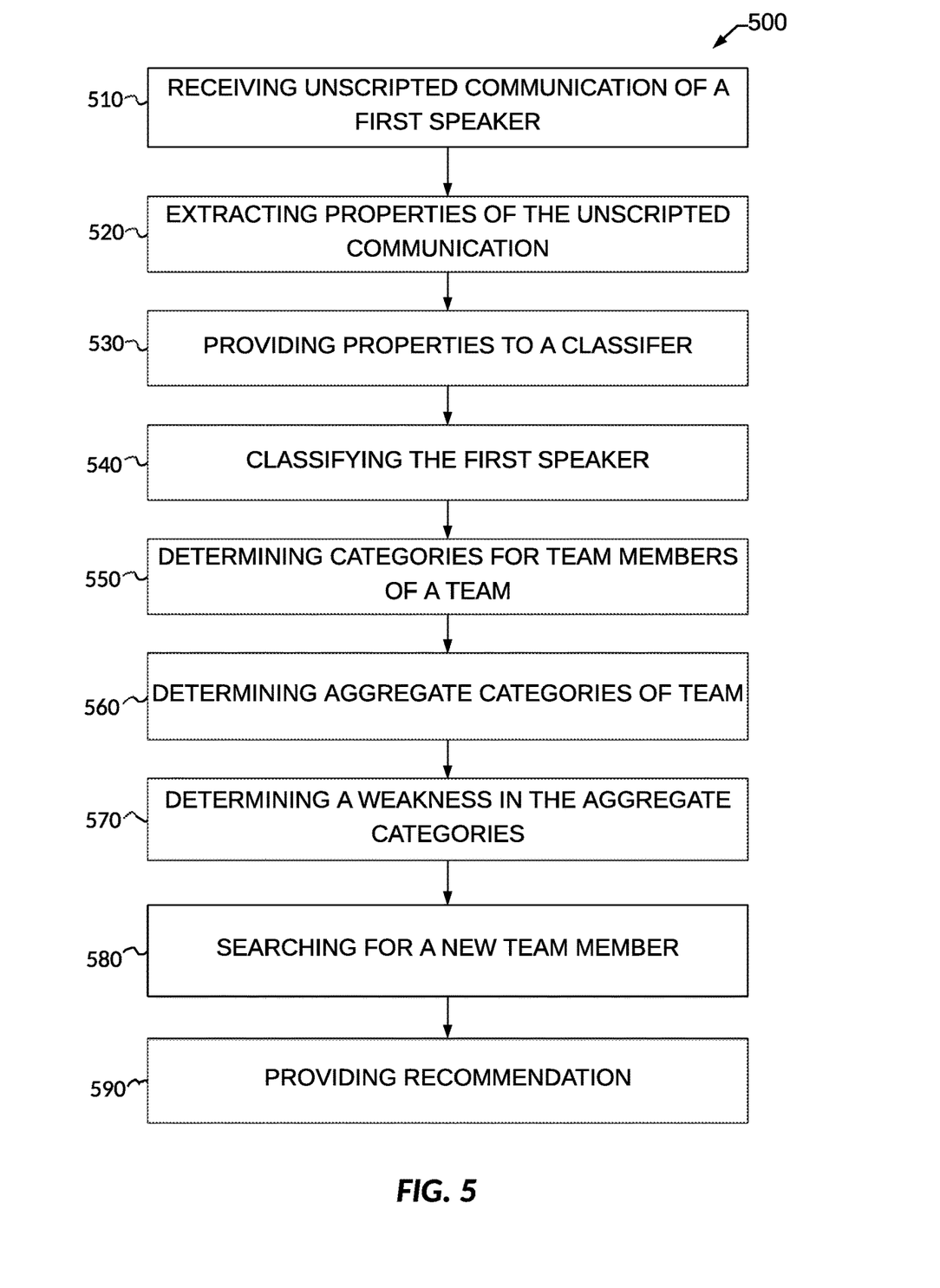
FIG. 5 is a flow diagram of a process for identifying team members in accordance with respective examples.

FIG. 5 is a flow diagram of a process 500 for identifying team members in accordance with respective example. The process 500 may be executed on a computing device. The process 500 may be used to identify candidates for a team that positively impact a team.

At 510, unscripted communication is received. The unscripted communication includes communication from a first speaker. The unscripted communication may include communication from recorded audio, electronic mail, chat sessions, and video conferences. At 520, properties of the unscripted communication are extracted. For example, the properties may be related to the first speaker. In an example, the properties may include properties related to the words spoken by the speaker, reactions from other individuals that are part of the conversation, etc. As another example, the extracted properties may include output of a sentiment analysis of the unscripted communication. As yet another example, the extracted properties may include a tone indication, a self-correction behavior score, and an indication of pauses between words based on an analysis of the unscripted communication.

At 530, the extracted properties are provided to a psychographic classifier. The psychographic classifier is trained on training data. At 540, the psychographic classifier classifies the first speaker into a psychographic category based on the extracted properties. The psychographic category may be a psychographic profile, a psychographic fingerprint, or a psychographic style score. At 550, the psychographic categories for each team member of a team are determined. The team does not include the first speaker. At 560, an aggregate psychographic category of the team is determined based on the psychographic categories of each of the team members of the team. At 570, a weakness in the aggregate psychographic category of the team is determined. At 580, a search is done to identify a new team member that has a psychographic category that addresses the weakness in the aggregate psychographic category of the team. In an example, the new team member is the first speaker. In another example, a group of candidate team members are identified based on the weakness in the aggregate psychographic category of the team. A candidate may then be selected for recommendation based on how the candidate further positively impacts the team's aggregate psychographic category. In another example, the candidates are ranked based on how much of a positive impact to the team's psychographic category the candidate would have. At 590, a recommendation that the first speaker become a team member of the team is provided.

In an example, to select a candidate a pool of candidates is received. For example, candidates that meet a certain criterion are received. Then each candidate's fingerprint is compared with the team's fingerprint. The overlap between the weak traits of a team fingerprint and strong traits of a candidate's fingerprint are determined. The candidates may then be ranked on the overlap. The candidate with the largest overlap may be selected as the recommended candidate.

In another example, correcting content is achieved. For example, content of a communication from the first speaker is received. The recipient of the communication may also be received. In some examples, the communication has not yet been sent to the recipient. The psychographic category of the recipient may be determined. The content may then be analyzed taking into account the psychographic category of the recipient. A suggestion for a change to the communication is determined based on the analysis. The change may automatically be implemented such that the communication is changed accordingly. For example, if the recipient is determined to respond well to praise based on the recipient's psychographic profile, the communication can be analyzed to determine if the communication includes a thank you and if a thank you is appropriate. If there is no thank you and one would be appropriate, a recommended correction is to include a thank you before the sender's signature.

In an example, the psychographic classifier is trained on a data set. For example, answers, from a plurality of test subjects, from a psychographic test are received. A psychographic category for each of the plurality of test subjects is determined. Second unscripted communication including communications from the plurality of test subjects is received. The psychographic classifier may be trained based on the psychographic categories of the plurality of test subjects and the second unscripted communications. The training data includes the psychographic category for each of the plurality of test subjects and the second unscripted communication.

In some example, the psychographic category of users is monitored based on real-time communications. For example, additional unscripted communication of the first speaker may be monitored. A current psychographic category of the first speaker may be determined based on the additional unscripted communication. The difference between the current psychographic category and the psychographic category may be determined. A message for the first speaker based on the difference is determined. The message may then be provided to the first speaker. For example, the current psychographic category of the first speaker may indicate that the first speaker is showing a higher score in seclusion. A message of encouragement may be sent to the first speaker based on the increase in the seclusion score.

As described above, relevant training material may be provided to employees based on the employee's psychographic category. As an example, training material that addresses the weakness in the aggregate psychographic category of the team is located. Access to the training material is provided to the members of the team. For example, relevant training materials may be located and then made available on a website accessible to members of the team. A communication providing a link to the training material may be provided to team members.

In various examples, multiple classifiers may be employed to determine the psychographic category of an individual. For example, some of the extracted properties may be provided to a second psychographic classifier. Classifying the first speaker into the psychographic category includes classifying, by the second psychographic classifier, the first speaker. The psychographic category may be a combination of the classification from both classifiers. In other examples, more than two classifiers may be used to create the psychographic category of the first speaker.

As described above, a profile may provide useful information regarding how an individual best receives and hears communications. In an example, based on the aggregate psychographic category of the team, a relevant input regarding communication styles is determined. Access to the relevant input is provided to the first speaker. For example, the team's psychographic category may indicate that the team is comprised of individuals that are great strategic thinkers but tend to not share all important details. This information may be determined and provided to the team members as a reminder to share relevant information. In addition, based on this input, communication between team members can be analyzed specifically looking for relevant information gaps. For example, is there data relevant to the group that is not being shared with all team members or is there a subgroup that shares information but not with the entire team. Identifying this information and the individuals with access to the data may be determined and provided to one or more team members. Appropriate correction may then take place. In an example, one correction may be providing a reminder to a team member to share information. This may occur when a team member is sending relevant information in a communication. The recipients of the communication may be determined and compared with the members of the team. If the communication appears to be a team communication and contains relevant information, if not all team members are on the communication a message to the sender may be displayed. The message may ask the sender if additional team members should be added to the communication. If the sender requests that the additional team members should be included, the missing team members may be added to the communication automatically. In addition, the message may indicate the relevant information and may indicate team members that do not appear to have received this information in previous communications.

Figure 6:
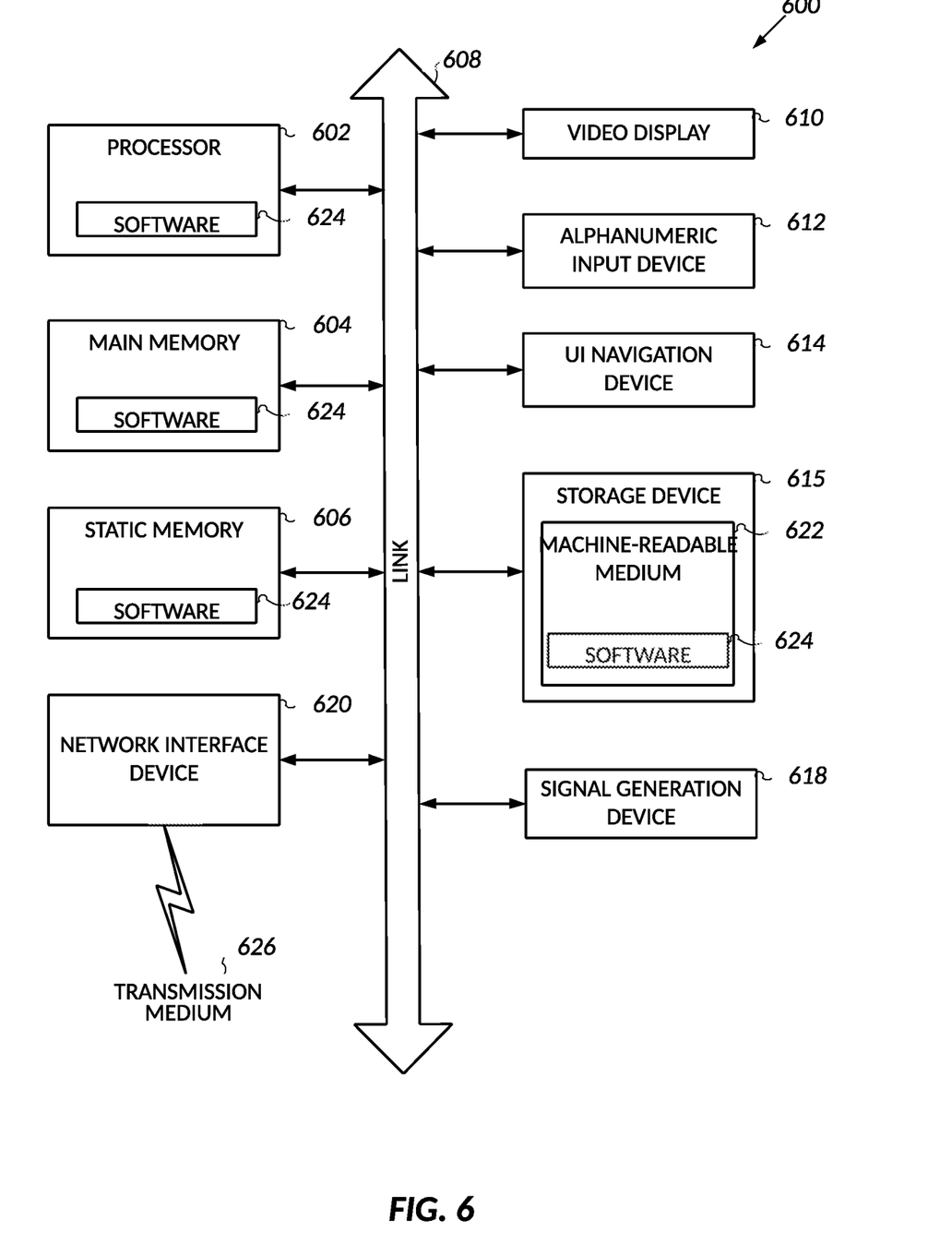
FIG. 6 is an example computing device that can be used in conjunction with the technologies described herein.

FIG. 6 is an example computing device that can be used in conjunction with the technologies described herein. In alternative embodiments, the computing device 600 may operate as a standalone device or may be connected (e.g., networked) to other computing devices. In a networked deployment, the computing device 600 may operate in the capacity of a server communication device, a client communication device, or both in server-client network environments. In an example, the computing device 600 may act as a peer computing device in peer-to-peer (P2P) (or other distributed) network environment. The computing device 600 may be a personal computer (PC), a tablet PC, a set top box (STB), a personal digital assistant (PDA), a mobile telephone, a smart phone, a web appliance, a network router, switch or bridge, or any computing device capable of executing instructions (sequential or otherwise) that specify actions to be taken by that computing device. Further, while only a single computing device is illustrated, the term "computing device" shall also be taken to include any collection of computing devices that individually or jointly execute a set (or multiple sets) of instructions to perform any one or more of the methodologies discussed herein, such as cloud computing, software as a service (SaaS), other computer cluster configurations. Computing device may be an implementation of device 500, may implement the privacy engine, may implement the location engine, perform the method of FIG. 8, and perform the method of FIG. 9.

Computing device 600 may include a hardware processor 602 (e.g., a central processing unit (CPU), a graphics processing unit (GPU), a hardware processor core, or any combination thereof), a main memory 604 and a static memory 606, some or all of which may communicate with each other via a link (e.g., bus) 608. The computing device 600 may further include a display unit 610, an input device 612 (e.g., a keyboard), and a user interface (UI) navigation device 614 (e.g., a mouse). In an example, the display unit 610, input device 612, and UI navigation device 614 may be a touch screen display. In an example, the input device 612 may include a touchscreen, a microphone, a camera (e.g., a panoramic or high-resolution camera), physical keyboard, trackball, or other input devices.

The computing device 600 may additionally include a storage device (e.g., drive unit) 616, a signal generation device 618 (e.g., a speaker, a projection device, or any other type of information output device), a network interface device 620, and one or more sensors, such as a global positioning system (GPS) sensor, compass, accelerometer, motion detector, or other sensor. The computing device 600 may include an input/output controller 628, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.) via one or more input/output ports.

The storage device 616 may include a computing-readable (or machine-readable) storage media 622, on which is stored one or more sets of data structures or instructions 624 (e.g., software) embodying or utilized by any one or more of the techniques or functions described herein. In an example, at least a portion of the software may include an operating system and/or one or more applications (or apps) implementing one or more of the functionalities described herein. The instructions 624 may also reside, completely or at least partially, within the main memory 604, within the static memory 606, and/or within the hardware processor 602 during execution thereof by the computing device 600. In an example, one or any combination of the hardware processor 602, the main memory 604, the static memory 606, or the storage device 616 may constitute computing device (or machine) readable media.

While the computer-readable storage media 622 is illustrated as a single medium, a "computer-readable storage media" or "machine-readable storage media" may include a single medium or multiple media (e.g., a centralized or distributed database, and/or associated caches and servers) configured to store the one or more instructions 624.

In an example, a computer-readable storage media or machine-readable storage media may include any medium that is capable of storing, encoding, or carrying instructions for execution by the computing device 600 and that cause the computing device 600 to perform any one or more of the techniques of the present disclosure, or that is capable of storing, encoding or carrying data structures used by or associated with such instructions. Non-limiting computer-readable storage media examples may include solid-state memories, and optical and magnetic media. Specific examples of computer-readable storage media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); and optical media disks. The computer-readable storage media is non-transitory in that the storage media does not consist of transitory propagating signals.

The instructions 624 may further be transmitted or received over a communications network 626 using a transmission medium via the network interface device 620 utilizing any one of a number of transfer protocols (e.g., frame relay, interne protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. The network interface device 620 may use the transfer protocols to transmit data using transitory propagating signals.

In an example, the network interface device 620 may include one or more physical jacks (e.g., Ethernet, coaxial, or phone jacks) or one or more antennas to connect to the communications network 626. In an example, the network interface device 620 may include one or more wireless modems, such as a Bluetooth modem, a Wi-Fi modem or one or more modems or transceivers operating under any of the communication standards mentioned herein. In an example, the network interface device 620 may include a plurality of antennas to wirelessly communicate using at least one of single-input multiple-output (SIMO), multiple-input multiple-output (MIMO), or multiple-input single-output (MISO) techniques. In some examples, the network interface device 620 may wirelessly communicate using Multiple User MIMO techniques. In an example, a transmission medium may include any intangible medium that is capable of storing, encoding or carrying instructions for execution by the computing device 600, and includes digital or analog communications signals or like communication media to facilitate communication of such software.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

The above description is intended to be illustrative, and not restrictive. For example, the above-described examples (or one or more aspects thereof) may be used in combination with others. Other embodiments may be used, such as by one of ordinary skill in the art upon reviewing the above description. Further, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A method comprising operations performed using an electronic processor, the operations comprising:
   receiving unscripted communication, the unscripted communication comprising communication from a first speaker;
   extracting properties of the unscripted communication related to the first speaker;
   providing the extracted properties to a psychographic classifier, wherein the psychographic classifier is trained on training data, wherein psychographic profiles of one or more individuals may be monitored by a personality insights analysis system, wherein the personality insights analysis system monitors changes to the psychographic profiles in real time as the psychographic profiles change based on additional unscripted communication which is provided to the psychographic classifier, wherein the additional unscripted communication comprises communication between at least two speakers, and wherein the at least two speakers comprise the first speaker;
   classifying, by the psychographic classifier, the first speaker into a psychographic category based on the extracted properties;
   determining the psychographic categories for each team member of a team, wherein the team does not comprise the first speaker;
   determining an aggregate psychographic category of the team based on the psychographic categories of each of the team members of the team;
   determining a weakness in the aggregate psychographic category of the team;
   searching for a new team member that has a psychographic category that addresses the weakness in the aggregate psychographic category of the team, wherein the new team member is the first speaker; and
   providing a recommendation that the first speaker become a team member of the team.

2. The method of claim 1, wherein the psychographic category comprises a fingerprint comprising a plurality of traits.

3. The method of claim 2, wherein the searching for a new team member comprises:
   receiving a plurality of team member candidates;
   determining, for each of the plurality of team member candidates, an overlap between weak traits of a team fingerprint and strong traits of a fingerprint of a team member candidate; and
   ordering the plurality of team member candidates based on the overlap.

4. The method of claim 3, wherein the first speaker has a highest overlap of the plurality of team member candidates.

5. The method of claim 1, further comprising:
   receiving an indication of a recipient of a communication;
   receiving content of the communication;
   determining a psychographic category of the recipient;
   analyzing the content of the communication based on the psychographic category of the recipient;
   identifying a correction in the content of the communication based on the analyzing of the content that is based on the psychographic category of the recipient.

6. The method of claim 1, further comprising:
   receiving answers, from a plurality of test subjects, from a psychographic test;
   determining a psychographic category for each of the plurality of test subjects;
   receiving second unscripted communication comprising communications from the plurality of test subjects; and
   training the psychographic classifier based on the psychographic categories of the plurality of test subjects and the second unscripted communications, wherein the training data comprises the psychographic category for each of the plurality of test subjects and the second unscripted communication.

7. The method of claim 1, wherein the unscripted communication comprises recorded audio, electronic mail, chat sessions, and video conferences.

8. The method of claim 1, further comprising:
monitoring additional unscripted communication of the first speaker;
determining a current psychographic category of the first speaker based on the additional unscripted communication;
determining a difference between the current psychographic category and the psychographic category; and
determining a message for the first speaker based on the difference.

9. The method of claim 1, further comprising:
searching for training material that addresses the weakness in the aggregate psychographic category of the team; and
providing access to the training material to the members of the team.

10. The method of claim 1, wherein the extracted properties comprise output of a sentiment analysis of the unscripted communication.

11. The method of claim 1, wherein the extracted properties comprise a tone indication, a self-correction behavior score, and an indication of pauses between words.

12. The method of claim 1, further comprises providing some of the extracted properties to a second psychographic classifier, wherein classifying the first speaker into the psychographic category further comprises classifying, by the second psychographic classifier, the first speaker.

13. The method of claim 1, further comprising:
determining, based on the aggregate psychographic category of the team, relevant input regarding communication styles; and
providing access to the relevant input to the first speaker.

14. A system comprising:
an electronic processor configured to:
receive unscripted communication, the unscripted communication comprising communication from a first speaker;
extract properties of the unscripted communication related to the first speaker;
provide the extracted properties to a psychographic classifier, wherein the psychographic classifier is trained on training data, wherein psychographic profiles of one or more individuals may be monitored by a personality insights analysis system, wherein the personality insights analysis system monitors changes to the psychographic profiles in real time as the psychographic profiles change based on additional unscripted communication which is provided to the psychographic classifier, wherein the additional unscripted communication comprises communication between at least two speakers, and wherein the at least two speakers comprise the first speaker;
classify, by the psychographic classifier, the first speaker into a psychographic category based on the extracted properties;
determine the psychographic categories for each team member of a team, wherein the team does not comprise the first speaker;
determine an aggregate psychographic category of the team based on the psychographic categories of each of the team members of the team;
determine a weakness in the aggregate psychographic category of the team;
search for a new team member that has a psychographic category that addresses the weakness in the aggregate psychographic category of the team, wherein the new team member is the first speaker; and
provide a recommendation that the first speaker become a team member of the team.

15. The system of claim 14, wherein the psychographic category comprises a fingerprint comprising a plurality of traits, and wherein the electronic processor to search for a new team member is configured to:
receive a plurality of team member candidates;
determine, for each of the plurality of team member candidates, an overlap between weak traits of a team fingerprint and strong traits of a fingerprint of a team member candidate; and
order the plurality of team member candidates based on the overlap.

16. The system of claim 15, wherein the first speaker has a highest overlap of the plurality of team member candidates.

17. The system of claim 14, wherein the electronic processor is further configured to:
receive an indication of a recipient of a communication;
receive content of the communication;
determine a psychographic category of the recipient;
analyze the content of the communication based on the psychographic category of the recipient; and
identify a correction in the content of the communication based on the analyzing of the content that is based on the psychographic category of the recipient.

18. The system of claim 14, wherein the electronic processor is further configured to:
receive answers, from a plurality of test subjects, from a psychographic test;
determine a psychographic category for each of the plurality of test subjects;
receive second unscripted communication comprising communications from the plurality of test subjects; and
train the psychographic classifier based on the psychographic categories of the plurality of test subjects and the second unscripted communications, wherein the training data comprises the psychographic category for each of the plurality of test subjects and the second unscripted communication.

19. A non-transitory computer-readable storage medium storing computer-executable instructions, the stored instructions comprising:
instructions to receive unscripted communication, the unscripted communication comprising communication from a first speaker;
instructions to extract properties of the unscripted communication related to the first speaker;
instructions to provide the extracted properties to a psychographic classifier, wherein the psychographic classifier is trained on training data, wherein psychographic profiles of one or more individuals may be monitored by a personality insights analysis system, wherein the personality insights analysis system monitors changes to the psychographic profiles in real time as the psychographic profiles change based on additional unscripted communication which is provided to the psychographic classifier, wherein the additional unscripted communication comprises communication between at least two speakers, and wherein the at least two speakers comprise the first speaker;

instructions to classify, by the psychographic classifier, the first speaker into a psychographic category based on the extracted properties;

instructions to determine the psychographic categories for each team member of a team, wherein the team does not comprise the first speaker;

instructions to determine an aggregate psychographic category of the team based on the psychographic categories of each of the team members of the team;

instructions to determine a weakness in the aggregate psychographic category of the team;

instructions to search for a new team member that has a psychographic category that addresses the weakness in the aggregate psychographic category of the team, wherein the new team member is the first speaker; and instructions to provide a recommendation that the first speaker become a team member of the team.

20. The non-transitory computer-readable storage medium of claim 19, wherein the psychographic category comprises a fingerprint comprising a plurality of traits, and wherein the instructions further comprise:

instructions to receive a plurality of team member candidates;

instructions to determine, for each of the plurality of team member candidates, an overlap between weak traits of a team fingerprint and strong traits of a fingerprint of a team member candidate; and instructions to order the plurality of team member candidates based on the overlap.

* * * * *